US009489703B2

(12) United States Patent
Kauniskangas et al.

(10) Patent No.: US 9,489,703 B2
(45) Date of Patent: Nov. 8, 2016

(54) TEST MANAGEMENT

(71) Applicant: iStoc Oy, Oulunsalo (FI)

(72) Inventors: Hannu Kauniskangas, Oulunsalo (FI);
Jarmo Jarvenpaa, Oulunsalo (FI)

(73) Assignee: IStoc Oy, Oulunsalo (FI)

( * ) Notice: Subject to any disclaimer, the term of this patent is extended or adjusted under 35 U.S.C. 154(b) by 313 days.

(21) Appl. No.: 14/190,414

(22) Filed: Feb. 26, 2014

(65) Prior Publication Data

US 2014/0247340 A1 Sep. 4, 2014

(30) Foreign Application Priority Data

Mar. 4, 2013 (FI) ...................................... 20135204

(51) Int. Cl.
*H04N 7/18* (2006.01)
*G06Q 50/22* (2012.01)
*G01N 21/84* (2006.01)
*G01N 21/78* (2006.01)

(52) U.S. Cl.
CPC ............... *G06Q 50/22* (2013.01); *G01N 21/78* (2013.01); *G01N 21/8483* (2013.01)

(58) Field of Classification Search
CPC .................... G01N 33/48771; G01N 33/5302; G01N 21/8483; H04N 7/183
See application file for complete search history.

(56) References Cited

U.S. PATENT DOCUMENTS 6,067,523 A * 5/2000 Bair .................... G06F 19/3487
705/2
6,295,506 B1 * 9/2001 Heinonen .......... A61B 5/14532
600/301
2004/0120557 A1 * 6/2004 Sabol ..................... G06Q 10/10
382/128
2006/0222567 A1 10/2006 Kloepfer et al.
2009/0223287 A1 * 9/2009 Dai ................... G01N 33/48771
73/64.56
2010/0254581 A1 10/2010 Neeser et al.
2012/0034598 A1 2/2012 Holmes et al.
2012/0274448 A1 * 11/2012 Marcus .............. G06K 19/0722
340/10.1
2013/0034908 A1 2/2013 Barstis et al.
2013/0189794 A1 * 7/2013 Emeric ............... B01L 3/50273
436/501

FOREIGN PATENT DOCUMENTS

| GB | 2497750 A | 6/2013 |
| WO | 2009054729 A1 | 4/2009 |
| WO | 2011137902 A1 | 11/2011 |
| WO | 2012131386 A1 | 10/2012 |

OTHER PUBLICATIONS

Finnish Search Report, dated Jan. 27, 2014, from corresponding FI application.

* cited by examiner

*Primary Examiner* — Huy T Nguyen
(74) *Attorney, Agent, or Firm* — Young & Thompson

(57) ABSTRACT

Computing resource and mobile test reader are disclosed. Computing resource receives from external entity related to test at least one parameter relating to test result generation of test belonging to certain manufacturing batch, and transmits at least one parameter to at least one mobile test reader. Mobile test reader receives from computing resource at least one parameter, configures test reader application with received at least one parameter, takes, with digital camera controlled by test reader application configured with at least one parameter, image data depicting output area test, and transmits test use feedback to computing resource.

13 Claims, 8 Drawing Sheets

TEST MANAGEMENT

FIELD

The invention relates to interaction between a computing resource and a mobile test reader apparatus.

BACKGROUND

Tests such as lateral flow tests are read with manufacturer-specific readers, but more generic apparatuses are currently emerging, one example being described in WO 2012/131386.

BRIEF DESCRIPTION

The present invention seeks to provide an improved computing resource and mobile test reader apparatus.

According to an aspect of the present invention, there is provided a computing resource comprising a data communication interface, one or more processors, and one or more memories including computer program code, the one or more memories and the computer program code configured to, with the one or more processors, cause the computing resource at least to perform: receive, from an external entity related to a test, with the data communication interface, at least one parameter relating to test result generation of the test belonging to a certain manufacturing batch; and transmit, with the data communication interface, the at least one parameter to at least one mobile test reader apparatus.

According to another aspect of the present invention, there is provided a mobile test reader apparatus comprising a digital camera, a wireless transceiver, a user interface, one or more processors, and one or more memories including computer program code, the one or more memories and the computer program code configured to, with the one or more processors, cause the mobile test reader apparatus at least to perform: receive, from a computing resource, with the wireless transceiver, at least one parameter relating to test result generation of a test belonging to a certain manufacturing batch; configure a test reader application with the received at least one parameter; take, with the digital camera controlled by the test reader application configured with the at least one parameter, image data depicting an output area of the test; and transmit, with the wireless transceiver, test use feedback to the computing resource.

LIST OF DRAWINGS

Example embodiments of the present invention are described below, by way of example only, with reference to the accompanying drawings, in which FIG. 1 illustrates an example embodiment of a general operating environment;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

It should be noted that while Figures illustrate various embodiments of apparatuses, they are simplified block diagrams that only show some structures and functional entities. The connections shown in these Figures are logical connections; the actual physical connections may be different. Interfaces between the various elements may be implemented with suitable interface technologies, such as a message interface, a method interface, a sub-routine call interface, a block interface, or any hardware/software means enabling communication between functional sub-units. It is apparent to a person skilled in the art that the described apparatuses may also comprise other functions and structures. It should be appreciated that details of some functions, structures, and the protocols used for communication are irrelevant to the actual invention. Therefore, they need not be discussed in more detail here. Although the apparatuses have been depicted as separate single entities, different parts may be implemented in one or more physical or logical entities.

Figure 1:
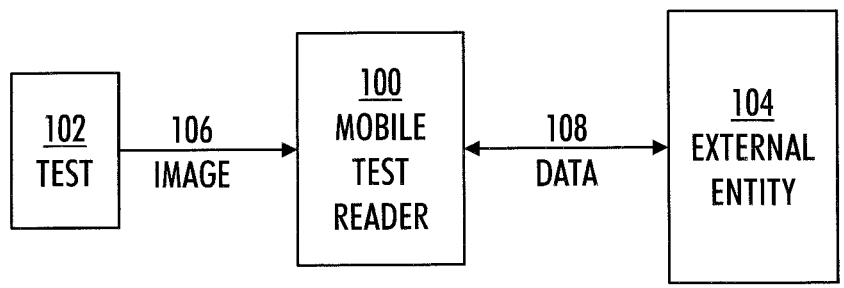

FIG. 1 illustrates an example embodiment of a general operating environment. A mobile test reader 100 takes an image 106 of a test 102. Furthermore, the mobile test reader 100 communicates data 108 relating to the test 102 with an external entity 104.

Figure 2:
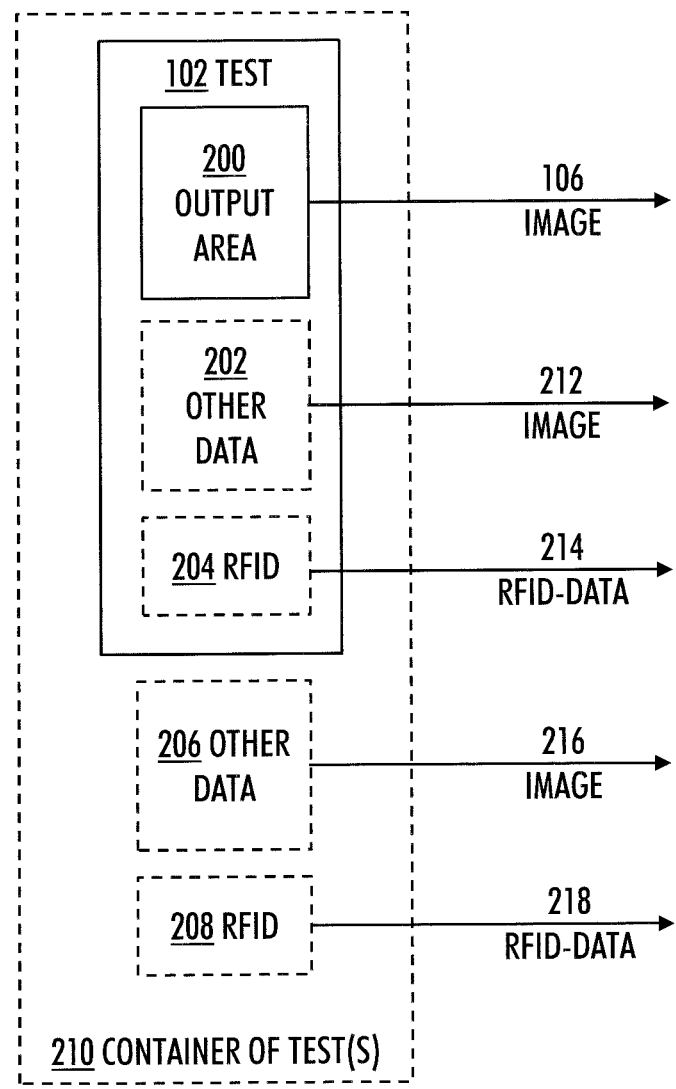
FIG. 2 illustrates example embodiments of a test.

FIG. 2 illustrates example embodiments of the test 102. The test 102 is capable of measuring a certain property of a target analyte in a sample. In its simplest form, the test 102 is capable of detecting the presence (or absence) of the target analyte in the sample. As the test 102 is relatively simple and cheap, it may be used for various diagnostics at home or in the field, for example, but also in clinics and laboratories.

The test 102 may be applied to human or animal secretions such as urine, saliva, blood, or stool samples, or also to other substances such as food or water. Accordingly, the test 102 may be utilized for medical testing of humans or animals, or testing food and water for contaminants, for example.

In an example embodiment, the test 102 is a (clinical) point of care test for pregnancy, fertility, HIV, coronary artery disease, malaria, drug abuse, respiratory disease, or for some other medical condition.

In an example embodiment, the test 102 may be a lateral flow test (also known as a lateral flow immunochromatographic assay).

The test 102 may comprise an output area 200 whose visual appearance changes to show the result of the test 102 in the form of the image 106. In the lateral flow test 102, the output area 200 may comprise at least one stripe, coupled by at least one capillary bed to a conjugate, the stripe changing colour as a result of a specified chemical reaction between a target molecule in the sample and its chemical partner in the conjugate.

In an example embodiment, the structure of the test 102 may also be hierarchical, meaning that it may include more than one parallel test, and even that one or more of the parallel tests may in turn include a number of subtests.

In an example embodiment, besides being the lateral flow test, the test 102 may be any test of at least one such chemical property that affects the visual appearance of the output area 200.

In an example embodiment, the test 102 may also comprise, besides the output area 102, other data 202 that may be visually inspected in the form of an image 212. The other data 202 may be read with a digital camera. The other data 202 may include text and/or symbols and/or images. The image 212 depicting the other data 202 may be interpreted with optical character recognition (OCR). The other data 202 may also include a barcode (linear or matrix barcode) such as a QR code, that may be interpreted with a digital camera and an appropriate software.

In an example embodiment, the test 102 may also comprise a radio frequency identifier (RFID) tag 204 capable of storing data that may be read 214 wirelessly.

In an example embodiment, a container 210 of the test 102 may comprise other data 206 that may be visually inspected in the form of an image 216, and/or a radio frequency identifier tag 208 capable of storing data that may be read 218 wirelessly. The container 210 may contain only one test 102 or a specific number of tests 102.

Figure 3:
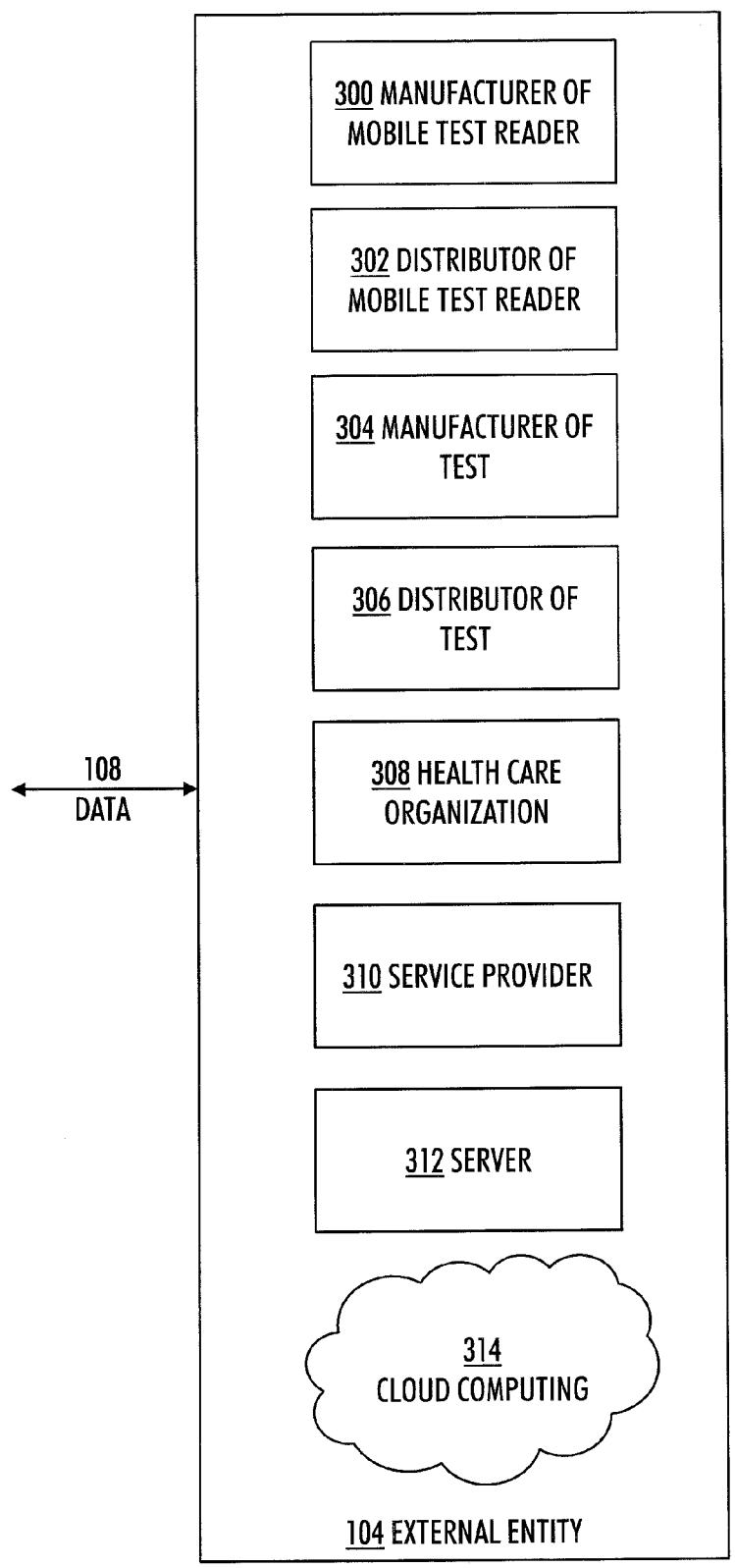
FIG. 3 illustrates example embodiments of an external entity.

FIG. 3 illustrates example embodiments of the external entity 104. The term "external entity" 104 refers to any interest group having a legitimate interest in the use of the test 102 and/or to any technical counterpart of the mobile test reader 100. Accordingly, a non-exhaustive list of the external entity 104 comprises at least one of the following: a manufacturer 300 of the mobile test reader 100, a distributor 302 of the mobile test reader 100, a manufacturer 304 of the test 102, a distributor 306 of the test 102, a health-care organization 308, a service provider 310, a server 312, a cloud computing 314. Naturally, the desired operating environment determines the rights of the various interest groups and the properties of the selected technical counterparts.

Figure 4:
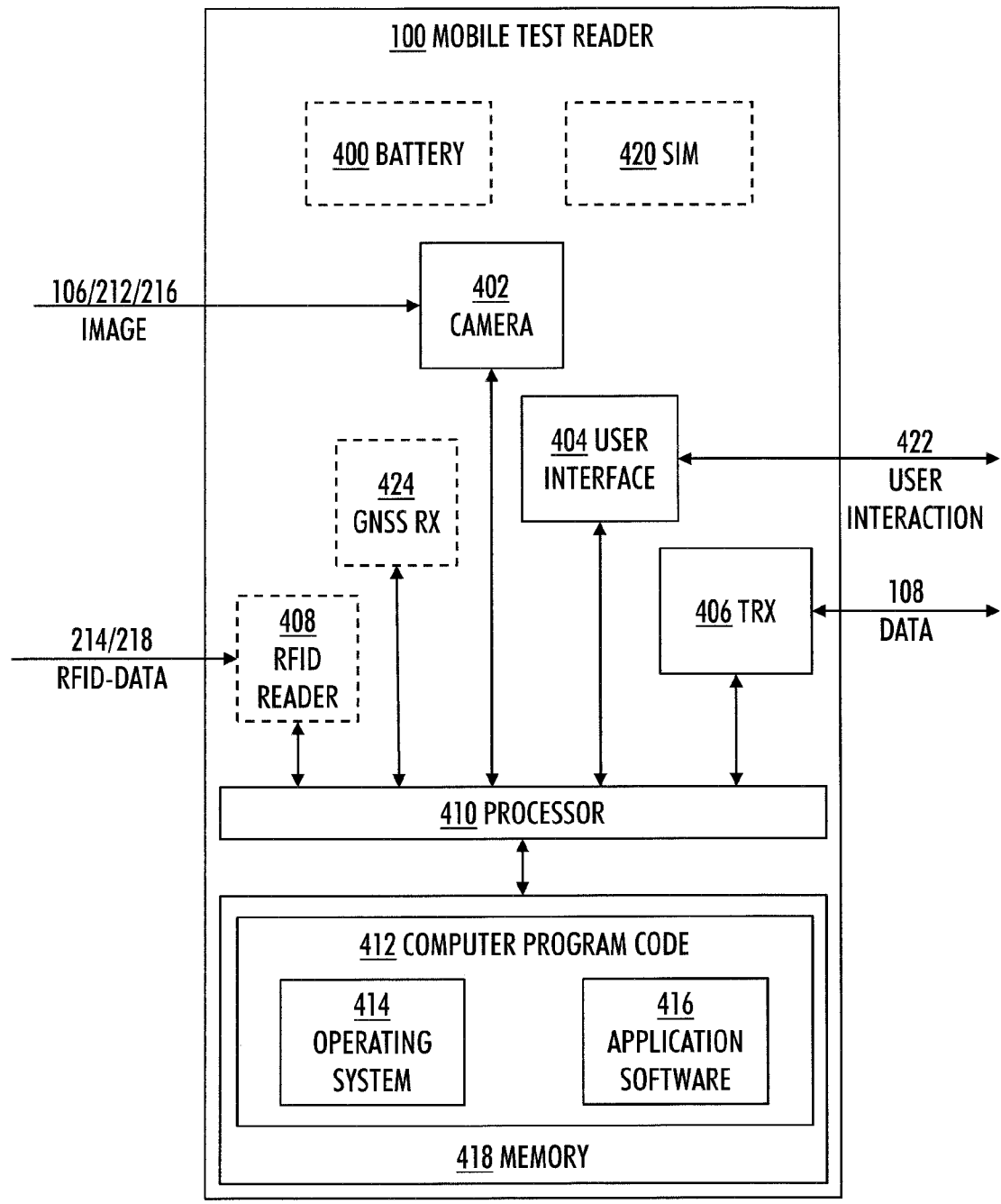
FIGS. 4, 5, 6 and 7 illustrate example embodiments of a mobile test reader.

FIG. 4 illustrates some example embodiments of the mobile test reader 100. The mobile test reader 100 may be any suitable mobile electronic apparatus. A non-exhaustive list of the types of the apparatus 100 includes: a mobile phone, a smartphone, a tablet computer, a general-purpose mobile computing device. In an example embodiment, the mobile test reader 100 is a general-purpose off-the-shelf computing device, as opposed to a purpose-build proprietary test reader, whereby research & development costs will be lower as only the special-purpose software (and not the hardware) needs to be designed, implemented and tested.

The mobile test reader 100 may comprise a battery 400, a digital camera 402, a user interface 404, a wireless transceiver 406, and a radio-frequency identifier reader 408.

In an example embodiment, the (rechargeable) electrical battery 400 is one or more electrochemical cells that convert stored chemical energy into electrical energy. Instead of battery 400, other suitable accumulator means may be used to store energy.

In an example embodiment, the digital camera 402 takes video or still photographs by recording images on an electronic image sensor through an optical system.

In an example embodiment, the user interface 404 implements the exchange 422 of graphical, textual and auditory information with the user of the mobile test reader 100. The user interface 404 may be realized with various techniques, such as a display, means for producing sound, a keyboard, and/or a keypad, for example. The display may be a liquid crystal display, for example, but it may also be implemented by any appropriate technique, such as with an active-matrix organic light-emitting diode. The display may also incorporate other user interaction means, such as touch input, or haptic feedback, i.e. the display may be a touch screen. The means for producing sound may be a loudspeaker or a simpler means for producing beeps or other sound signals. The keyboard/keypad may comprise a complete (QWERTY) keyboard, a mere numeric keypad or only a few push buttons and/or rotary buttons. In addition, the user interface 404 may comprise other user interface components, for example various means for focusing a cursor (mouse, track ball, arrow keys, touch sensitive area etc.) or elements enabling audio control.

In an example embodiment, the wireless transceiver 406 may be interoperable with various wireless standard/non-standard/proprietary communication networks such as any mobile phone network, regardless of the generation (such as 2G, 3G, 4G, beyond 4G, etc.) such as GSM (Global System for Mobile Communications), GPRS (General Packet Radio Service), EGPRS (Enhanced GPRS), WCDMA (Wideband Code Division Multiple Access), UMTS (Universal Mobile Telephone System), 3GPP (The 3rd Generation Partnership Project), IMT (International Mobile Telecommunication), LTE (Long Term Evolution, LTE-A (LTE-Advanced), and other radio systems (in their present forms and/or in their evolution forms), such as WLAN (Wireless Local Area Network) based on IEEE (Institute of Electrical and Electronics Engineers) 802.11 standard or its evolution versions (IEEE 802.11ac etc.), WiMAX (Worldwide Interoperability for Microwave Access, or Wi-Fi, for example.

In an example embodiment, the wireless transceiver 406, while communicating with a mobile phone network, may require a subscriber identity module (SIM) 420, which may be an integrated circuit storing subscriber data, which is network-specific information used to authenticate and identify subscribers on the cellular network. The subscriber identity module may be embedded into a removable SIM card, on a mini-SIM card, for example. Furthermore, the mobile test reader 100 may include a SIM card reader (not illustrated in FIG. 4), for example. Besides being implemented on a SIM card, the subscriber identity module 420 may be implemented with other techniques as well, such as a virtual/embedded SIM.

In an example embodiment, the mobile test reader 100 includes a RFID reader 408 capable of reading RFID data 214 218 programmed into the electronic tag 204, 208 of the test 102 or its container 210. The reader 408 reads 214, 218 the data from the tag 204, 208 with radio waves. The tag 204, 208 may comprise at least two parts: an integrated circuit for storing and processing information, modulating and demodulating a RF signal, and other specialized functions, and an antenna for receiving and transmitting the signal. The tag 204, 208 may be passive (using no battery), active (with a battery and always broadcasting its signal) or battery assisted passive (with a battery and activated by the presence of the reader 408). In an example embodiment, near field communication (NFC) may be utilized. NFC is a set of standards for smartphones and similar devices to establish radio communication with each other by touching them together or bringing them into close proximity. NFC utilizes various short-range wireless technologies, typically requiring a distance of four centimetres or less. In NFC, the reader 408 is also known as an initiator generating a radio frequency field powering and reading 214, 218 the data from the external object 204, 208 also known as a passive target.

The mobile test reader 100 also comprises one or more processors 410, and one or more memories 418 including computer program code 412.

In an example embodiment, the term 'processor' 410 refers to a physical device that is capable of processing data in a computer or other digital electronic device. Depending on the processing power needed, the mobile test reader 100 may comprise several processors 410 such as parallel processors or one or more multicore processors. A non-exhaustive list of implementation techniques for the processor 410 includes, but is not limited to: logic components, standard integrated circuits, application-specific integrated circuits (ASIC), system-on-a-chip (SoC), application-specific standard products (ASSP), microprocessors, digital signal processors, special-purpose computer chips, and field-programmable gate arrays (FPGA).

In an example embodiment, the term 'memory' 418 refers to a physical device that is capable of storing the computer program code 412 and data on a temporary or permanent basis for use in a computer or other digital electronic device. In an example embodiment, the term 'memory' refers to working memory (also known as primary storage, main memory or internal storage) directly accessible to the processor. In an example embodiment, the working memory may be implemented as a random-access memory (RAM), such as a dynamic RAM, DRAM.

In an example embodiment, the computer program code 412 includes an operating system 414 and application software 416. The operating system may be Android, Microsoft Windows Phone, Apple iOS, Linux, or Symbian, for example. The application software 416 includes all the applications running in the mobile test reader 100.

Naturally, the mobile test reader 100 may include a number of other components, but as they are not required to illustrate the present embodiments, they will not be further described.

Figure 5:
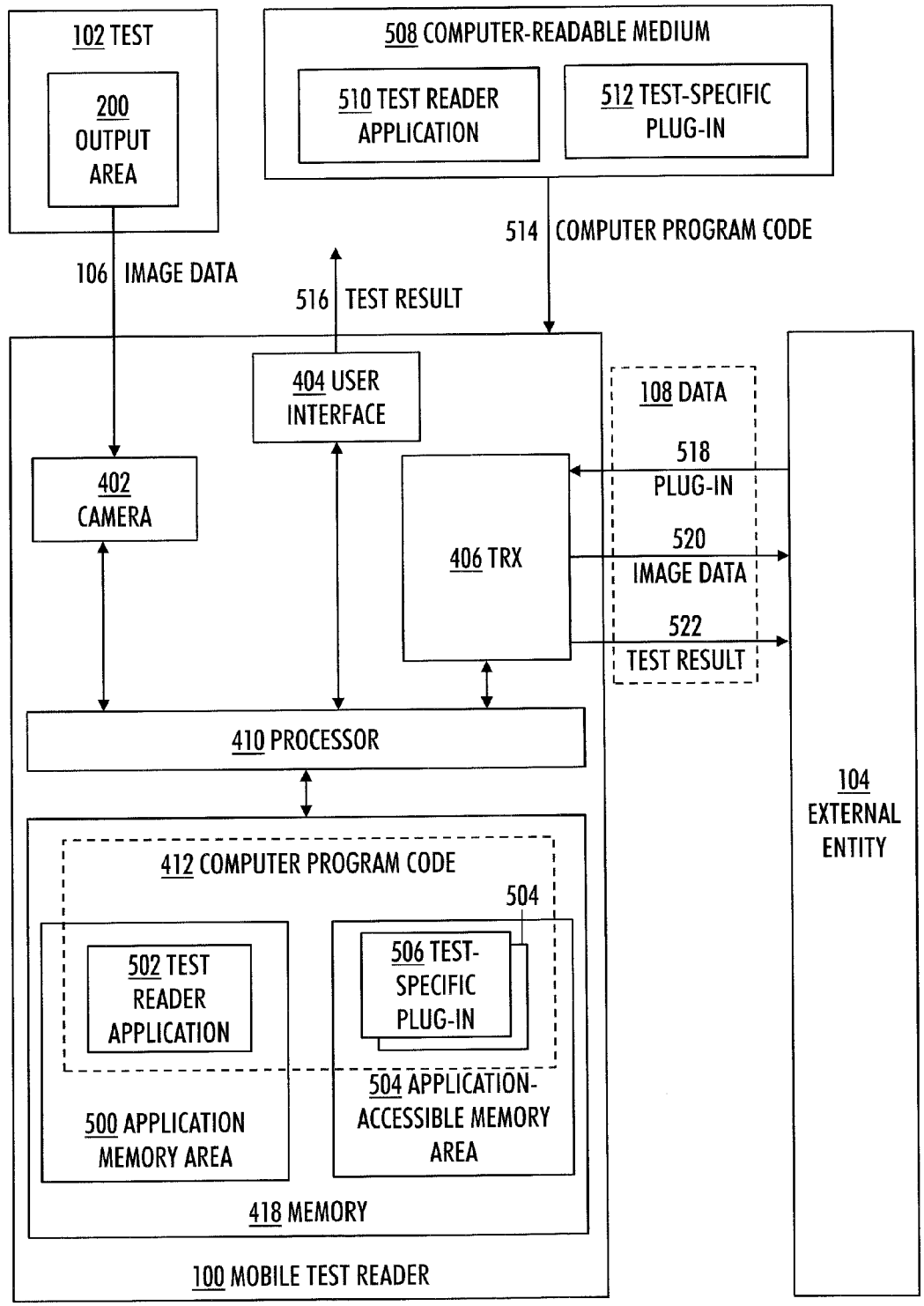

Let us next study FIG. 5, illustrating further example embodiments of the mobile test reader 100, especially the way the mobile test reader 100 interacts with the test 102 and the external entity 104.

In an example embodiment, the one or more memories 418 and the computer program code 412 are configured to, with the one or more processors 410, cause the mobile test reader 100 to receive, with the wireless transceiver 406, a test-specific plug-in 518 from the external entity 104, to configure a test reader application 502 with the received test-specific plug-in 506, and to take, with the digital camera 402 controlled by the test reader application 502 configured with the test-specific plug-in 506, image data 106 depicting the output area 200 of the test 102.

With this mechanism, the test reader application 502 may be configured with various test-specific plug-ins 506, 504, i.e., the memory 418 may contain different test-specific plug-ins, one for each different type of test 102.

In an example embodiment, the test-specific plug-in 506 comprises at least some of the following information:
- an image taking instruction for taking of the image data 106 with the digital camera 402, the image taking instruction comprising at least one of the following: manual/automatic mode, focus distance, location, focus, lighting, shooting angle;
- an analysis instruction for analysis of the output area 200, the analysis instruction comprising at least one of the following: optical readability, colour info, ratiometric numbers, a test limit parameter, a test criteria, a test reliability parameter, a test quality parameter, a test validity parameter;
- general information on the test 102, the general information comprising at least one of the following: an identifier of a manufacturing batch of the test 102, a manufacturer identifier, a manufacturing date of the test 102, information on the quality of the production batch of the test 102, information on the use by date of the test 102, information on the dimensions or relative dimensions of the output area 200, information on the dimensions or relative dimensions of the test 102.

Naturally, the above described information for the test-specific plug-in 506 is just a non-limiting example embodiment. Furthermore, the following information may or may not be present in the test-specific plug-in: a test 102 identifier, a name for the test 102, a name in the local language(s) for the test 102, an image analysis algorithm, a flashlight instruction (on/off/intensity), a bounding box (=an area within which the output area 200 is searched for), size and location of an aiming crosshair (or box, or other aiming aid) for the output area 200, size of the output area 200 in pixels, a minimum and maximum aspect ratio between the breadth and height of the output area 200, a minimum and maximum intensity of the stripe(s) in the output area 200, location of the stripe(s) in the output area 200, a reliability threshold for successive similar video frames, a maximum allowable deviation for the shooting angle in roll and pitch directions, an offset for said maximum allowable deviation, test 102 interpretation rules, workflow rules for the test 102. The workflow rules for the test 102 may include various information relating to the correct workflow of the testing procedure. The workflow rule may determine that the test 102 result needs to be read after a predetermined time period (5 minutes, for example) from the insertion of the sample in the test 102. The workflow rule may determine when the test result may be shown to the user: immediately, or after a medical doctor or other authority has examined the test 102 result.

Furthermore, in an example embodiment, the one or more memories 418 and the computer program code 412 are further configured to, with the one or more processors 410, under the control of the test reader application 502 configured with the test-specific plug-in 506, cause the mobile test reader 100 further to perform at least one of the following: transmit, with the wireless transceiver 406, the image data 520 to the external entity 104; generate, with the test reader application 502 configured with the test-specific plug-in 506, a test result for the test 102 on the basis of the image data 106; transmit, with the wireless transceiver 406, the test result 522 to the external entity 104; output, with the user interface 404, the test result 516. This means that the mobile test reader 100 may just transmit the image data 520 to the external entity 104, whereupon the external entity 104 generates the test result. Or it may mean that the test result is generated in the mobile test reader 100, and the test result is shown to the user and/or transmitted to the external entity 104. Even though the test result is generated in the mobile test reader 100, the image data 520 may still be transmitted to the external entity 104 as well.

In an example embodiment, the one or more memories 418 comprises an application memory area 500 and an application-accessible memory area 504. The computer program code of the test reader application 502 may be stored in the application memory area 500. The one or more memories 418 and the computer program code 412 may further be configured to, with the one or more processors 410, cause the mobile test reader 100 to store the received test-specific plug-in 506 in the application-accessible memory area 504.

In an example embodiment, the one or more memories 418 and the computer program code 412 are further configured to, with the one or more processors 410, cause the mobile test reader 100 to store the received test-specific plug-in 506 in the application-accessible memory area 504 without having to exercise any control by an authority other than the user of the mobile test reader 100.

In an example embodiment, the one or more memories 418 and the computer program code 412 are further configured to, with the one or more processors 410, cause the mobile test reader 100 to configure the test reader application 502 with the test-specific plug-in 506 without having to restart the mobile test reader 100 and/or the test reader application 502.

In an example embodiment, the one or more memories 418 and the computer program code 412 are further configured to, with the one or more processors 410, cause the mobile test reader 100 to configure the test reader application 502 with the test-specific plug-in 506 automatically, i.e. without any user interaction, or with the user confirming the operation. Optionally, the user may be informed that the update of the test-specific plug-in 506 has been made.

Figure 6:
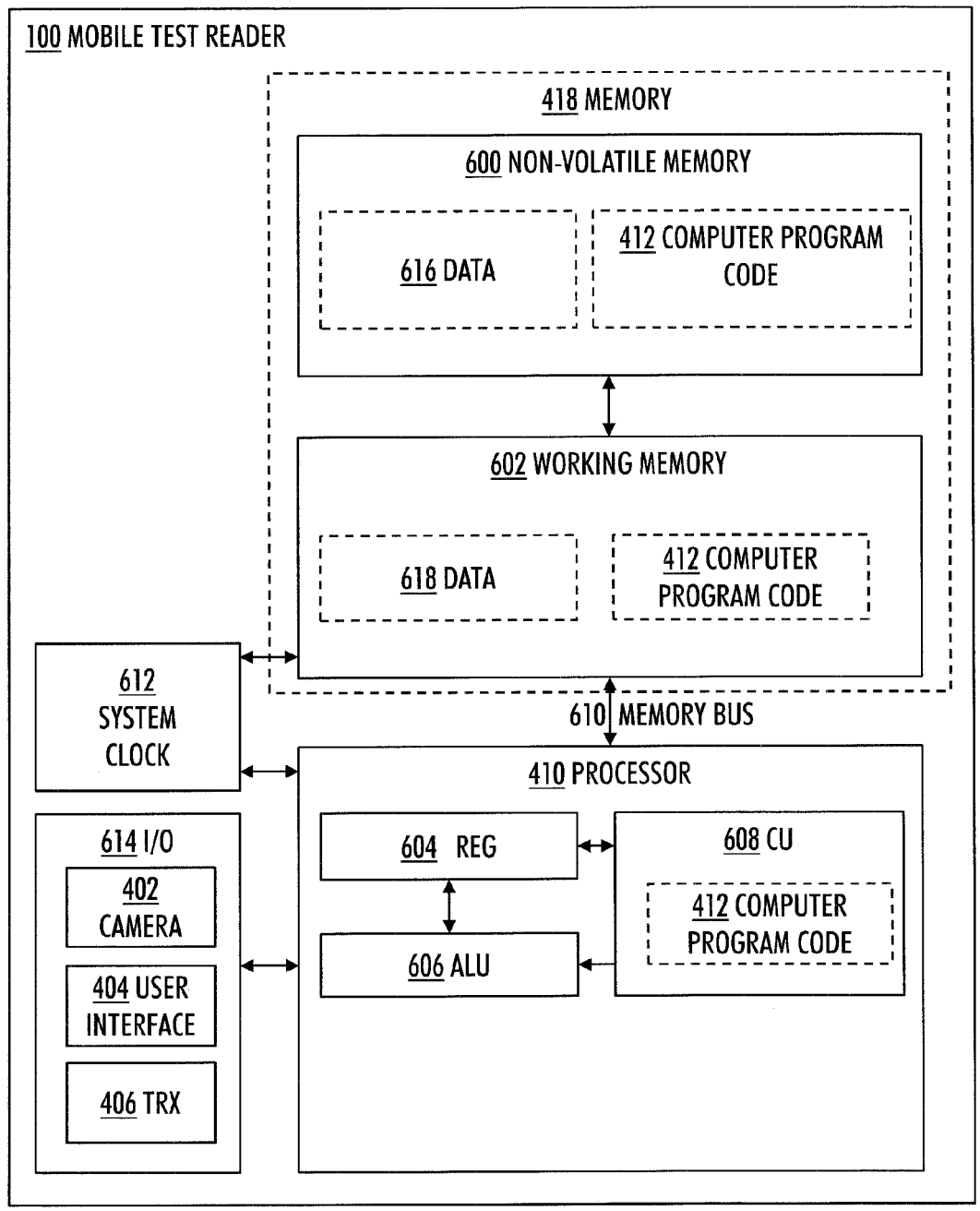

In an example embodiment illustrated in FIG. 6, the mobile test reader 100 may be an electronic digital computer, which may comprise a non-volatile memory 600 and a working memory 602 as the memory 418, the processor 410, a system clock 612 and an input/output 614 including the digital camera 402, the user interface 404, and the wireless transceiver 406. Naturally, the computer may comprise a number of other peripheral devices, not illustrated here for the sake of clarity. Also, the architecture of FIG. 6 is just one example embodiment as other feasible computing architectures may be utilized as well to implement the hardware and software of the mobile test reader 100.

In an example embodiment, the system clock 612 constantly generates a stream of electrical pulses, which cause the various transferring operations within the computer to take place in an orderly manner and with specific timing.

In an example embodiment, the processor 410 may be implemented as a microprocessor implementing functions of a central processing unit (CPU) on an integrated circuit. The CPU 410 is a logic machine executing the computer program code 412. The computer program code 412 may be coded as a computer program using a programming language, which may be a high-level programming language, such as C, C++, or Java, or a low-level programming language, such as a machine language, or an assembler. There are many ways to structure the computer program code 412 In an example embodiment, the operations of the computer program code 412 may be divided into functional modules, sub-routines, methods, classes, objects, applets, macros, etc., depending on the software design methodology and the programming language used. In modern programming environments, there are software libraries, i.e. compilations of ready-made functions, which may be utilized by the computer program code 412 for performing a wide variety of standard operations.

The CPU 410 may comprise a set of registers 604, an arithmetic logic unit (ALU) 606, and a control unit (CU) 608. The control unit 608 is controlled by the computer program code 412 transferred to the CPU 410 from the working memory 602. The working memory 602 is directly or indirectly connected to the CPU 410 via a memory bus 610 including two buses: an address bus and a data bus. The CPU 410 sends a memory address indicating the desired location of data 618 (such as the image data 106, or data 108) or computer program code 412 through the address bus, whereupon the CPU 410 reads or writes the data itself from/to the working memory 602 using the data bus.

The control unit 608 may contain a number of microinstructions for basic operations. The implementation of the microinstructions may vary, depending on the CPU design. The microprocessor 410 may also have an operating system (such as a general-purpose operating system), which may provide the computer program code 412 with system services. During running of the computer program code 412, the computer program code 412 or a part of it are transferred via the memory bus 610 from the working memory 602 into the control unit 608, wherein usually a portion of the computer program code 412 resides and controls the operation.

In an example embodiment, the non-volatile memory 600 retains the stored information even when not powered. Examples of non-volatile memory include read-only memory (ROM), flash memory, magnetic computer storage devices such as hard disk drives, and optical discs. As is shown in FIG. 6, the non-volatile memory 600 may store both data 616 and the computer program code 412.

An example embodiment, illustrated in FIG. 5, provides a computer readable medium 508 comprising the computer program code 412 of the test reader application 510 and the test-specific plug-in 512. Said computer program code 412, when executed on the mobile test reader 100, causes the mobile test reader 100 to perform the operations required to implement the described example embodiments. In an example embodiment, the computer program code 412 may be in source code form, object code form, or in some intermediate form. The computer-readable medium 508 may comprise at least the following: any entity or device capable of carrying 514 computer program code 412 to the mobile test reader 100, a record medium, a computer memory, a read-only memory, an electrical carrier signal, a telecommunications signal, and a software distribution medium. In some jurisdictions, depending on the legislation and the patent practice, the computer-readable medium 508 may not be the telecommunications signal. In an example embodiment, the computer-readable medium 508 may be a non-transitory computer readable storage medium.

Figure 7:
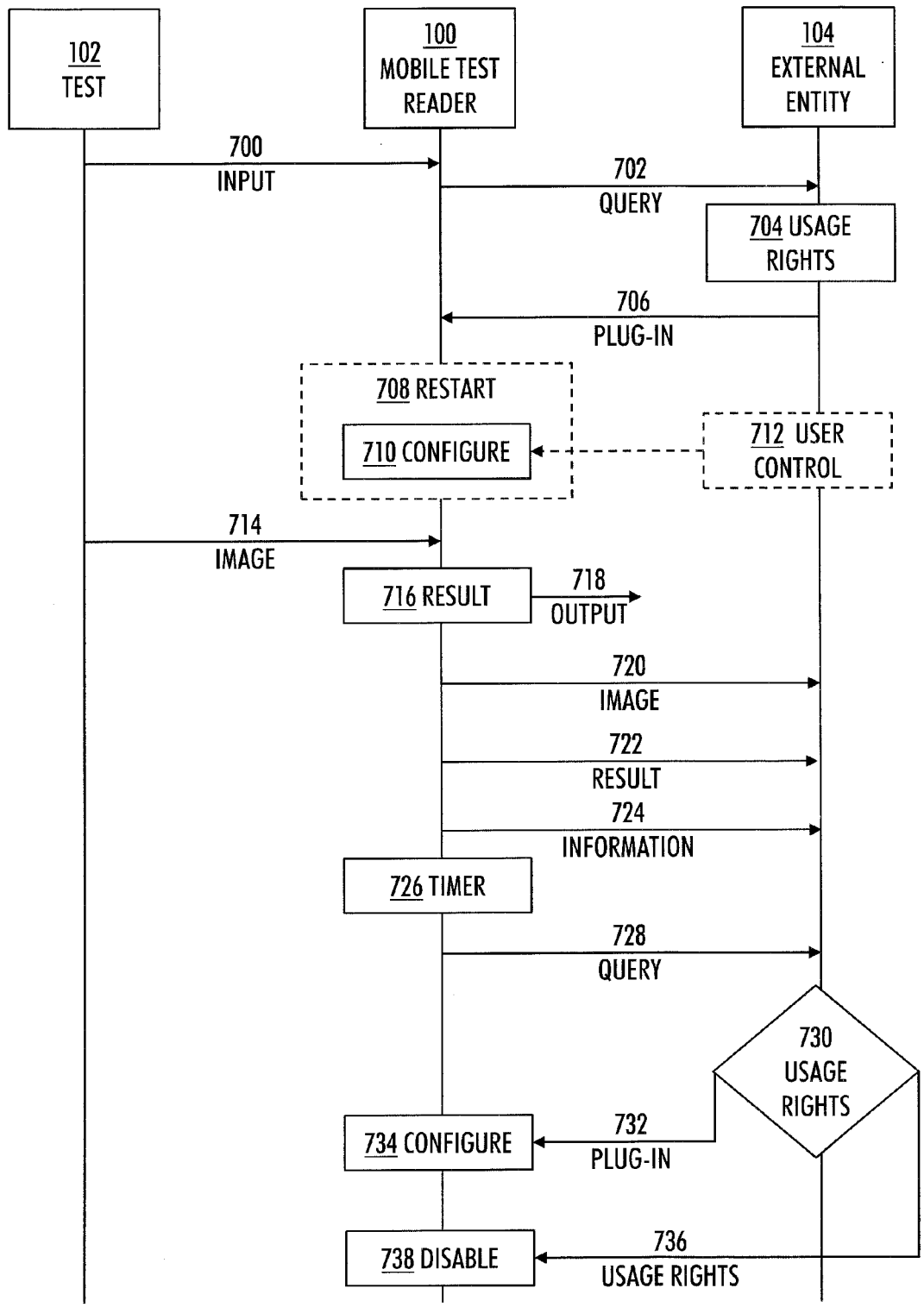

Next, with reference to FIG. 7, let us study the communication of the mobile test reader 100 and some further example embodiments in the form of a signal sequence chart. Other functions, not described in this application, may also be executed between the operations or within the operations. Some of the operations or parts of the operations may also be left out or replaced by a corresponding operation or part of the operation.

In an example embodiment, the mobile test reader 100 inputs 700, with the digital camera 402 or with the user interface 404, or with a wireless reading (with the RFID reader 408), an identifier of the test 102 and/or type of the test 102 to the test reader application 502.

In an example embodiment, the mobile test reader 100, prior to receiving the test-specific plug-in 506 from the external entity 104, transmits 702, with the wireless transceiver 406, a query to the external entity 104 regarding the test-specific plug-in 506, the query including the present status of the test-specific plug-in 506, the present status indicating the presence of the test-specific plug-in 506, and/or or the version number of the test-specific plug-in 506. If the test-specific plug-in 506 is present, the version number may be transmitted, but if the test-specific plug-in is missing, only the presence information may be transmitted.

In an example embodiment, the mobile test reader 100 transmits, with the wireless transceiver 406, information relating to the mobile test reader 100 to the external entity 104, the information relating to the mobile test reader 100 including at least one of the following: type of the mobile test reader 100, location of the mobile test reader 100, local time of the mobile test reader 100, information on the climatic conditions surrounding the mobile test reader 100.

As illustrated in FIG. 4, in order to determine its location, the mobile test reader 100 may comprise a positioning receiver 424 receiving external location information, which may be utilized to generate location of the mobile test reader 100. The positioning receiver 424 may be a receiver of a global navigation satellite system (GNSS). Such a system may be the Global Positioning System (GPS), the Global Navigation Satellite System (GLONASS), the Galileo Positioning System (Galileo), the Beidou Navigation System, The Quasi-Zenith Satellite System (QZSS), or the Indian Regional Navigational Satellite System (IRNSS), for example. The positioning receiver 424 determines its location (longitude, latitude, and altitude) using signals transmitted from satellites orbiting the earth. Besides global navigation satellites, the positioning receiver 424 may also determine its location by utilizing other known positioning techniques. It is well known that by receiving radio signals from several different base stations, a mobile phone may determine its location, for example.

FIG. 7 also illustrates the earlier described basic sequence: the mobile test reader 100 receives 706, with the wireless transceiver 406, the test-specific plug-in 518 from the external entity 104, configures 710 the test reader application 502 with the received test-specific plug-in 506, and takes 714, with the digital camera 402 controlled by the test reader application 502 configured with the test-specific plug-in 506, image data 106 depicting the output area 200 of the test 102.

It is to be noted, as was explained earlier, that in an example embodiment the mobile test reader 100 stores the received test-specific plug-in 506 in the application-accessible memory area 504 without having to exercise any control 712 by an authority other than the user of the mobile test reader 100. The mobile test reader 100 also configures in an example embodiment the test reader application 502 with the test-specific plug-in 506 without having to restart 708 the mobile test reader 100 and/or the test reader application 502. Accordingly, reference numerals 708 and 712 depict such operations that are not required at all in certain example embodiments.

The earlier described basic sequence continues in FIG. 7 as follows: the mobile test reader 100, under the control of the test reader application 502 configured with the test-specific plug-in 506, performs at least one of the following: transmits 720, with the wireless transceiver 406, the image data 520 to the external entity 104; generates 716, with the test reader application 502 configured with the test-specific plug-in 506, a test result for the test 102 on the basis of the image data 106; transmits 722, with the wireless transceiver 406, the test result 522 to the external entity 104; outputs 718, with the user interface 404, the test result 516. As was explained earlier, also other information 724 may be transmitted from the mobile test reader 100 to the external entity 104.

In an example embodiment, the mobile test reader 100 receives 706, with the wireless transceiver 406, the newest version of the test-specific plug-in 506, and configures 710 the test reader application 502 with the newest version of the test-specific plug-in 506.

The configuring of the test reader application 502 with the test-specific plug-in 506 may be performed as required.

When the mobile test reader 100 prepares for reading the test 102, it queries 702 the external entity for the test-specific plug-in 506, either for the first time, or for the latest version. FIG. 7 also illustrates another example embodiment, the mobile test reader 100 may include a timer mechanism 726, with which the mobile test reader 100 is able to query for the newest version of the test-specific plug-in at predetermined intervals (every five minutes, for example) or at predetermined times (once a day or week at noon, for example). The external entity 104 may also transmit the test-specific plug-in 506 to the mobile test reader 100 without any stimulus received from the mobile test reader 100, with a push mechanism, for example.

In an example embodiment, the mobile test reader 100 manages, with the test reader application 502 the usage rights 704, 730 of the test 102 such that the test-specific plug-in 506 is removed if no usage rights exist for the test 102 on the basis of information received from the external entity 104 with the wireless transceiver 406.

In an example embodiment, the mobile test reader 100 transmits 728, with the wireless transceiver 406, hardware identifier of the mobile test reader 100 and/or user account information of the user of the mobile test reader 100 to the external entity 104, and receives 732/736, with the wireless transceiver 406, usage rights of the test-specific plug-ins 506, 504.

In an example embodiment, the external entity 104 keeps 730 track of the usage rights of the test 102, whereby, if the usage rights exists, the external entity 104 transmits 732 the test-specific plug-in to the mobile test reader 100, whereupon the mobile test reader 100 configures 734 the test reader application 502 with the test-specific plug-in 506, or, if the usage rights do not exist, the external entity 104 only transmits 738 usage rights information to the mobile test reader 100, whereupon the mobile test reader 100 disables 738 the test-specific plug-in 506, if such is present in the mobile test reader 100. The disable-function 738 may just make the test-specific plug-in 506 inoperable, or it may remove the test-specific plug-in 506 altogether.

In an example embodiment, the mobile test reader 100 calculates a check-sum for the present test-specific plug-ins 506, 504, and the check-sum is transmitted to the external entity 104. The external entity 104 maintains an account for each mobile test reader 100, i.e. usage rights of each mobile test reader 100 for the test-specific plug-ins 506, 504. If the check-sum that is in the account matches with the check-sum that is received from the mobile test reader 100, the external entity 104 determines that no update is required. However, if the check-sums do not match, the external entity 104 initiates the required operations as regards to the usage rights: either a new plug-in is transmitted to the mobile test reader 100, some or all plug-ins are updated, or one or more plug-ins are made inoperable or even removed from the mobile test reader 100, for example.

Figure 8:
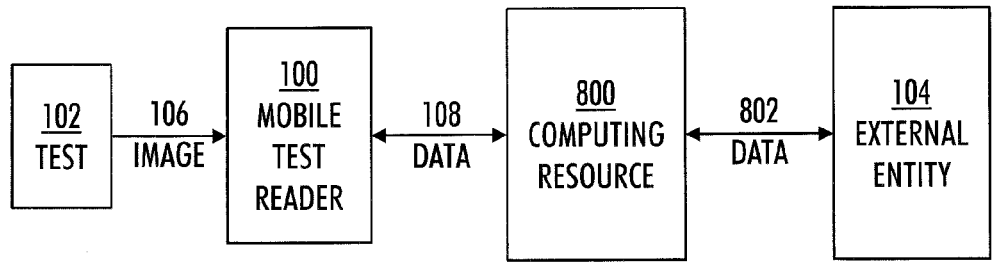
FIGS. 8 and 9 illustrate further example embodiments of the general operating environment.

Next, FIG. 8 illustrates another example embodiment of the general operating environment. This has already been illustrated in FIG. 1, but now some modifications are made to obtain further technical advantages. The mobile test reader 100 takes the image 106 of the test 102. But now the mobile test reader 100 communicates data 108 relating to the test 102 with a computing resource 800, and the computing resource communicates data 802 with the external entity 104.

Figure 9:
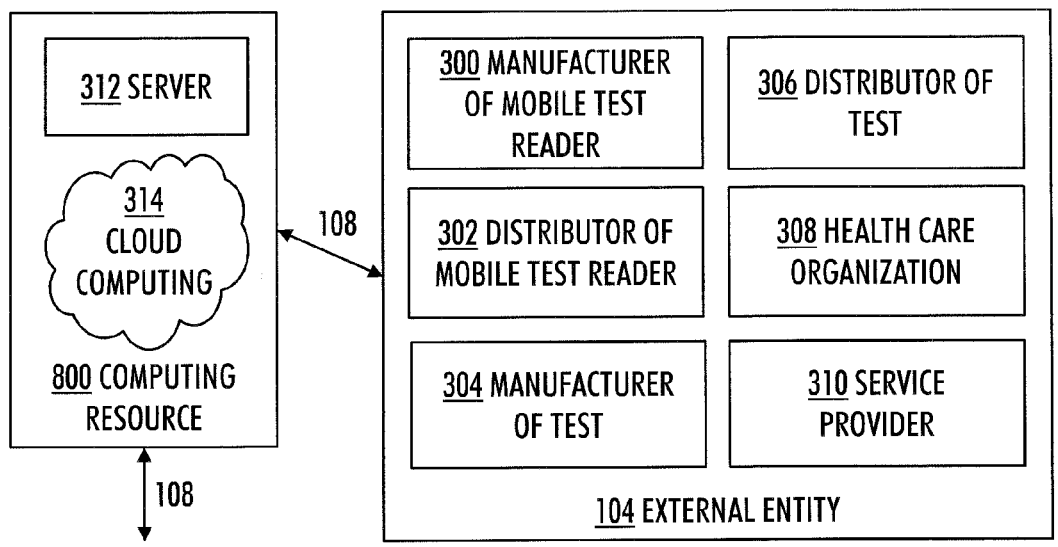

FIG. 9 illustrates example embodiments of the external entity 104 and the computing resource 800. The external entity 104 has already been illustrated in FIG. 3, but now the external entity 104 and the computing resource 800 have been separated to obtain further technical advantages. The term "external entity" 104 refers to any interest group having a legitimate interest in the use of the test 102, but the term "computing resource" 800 refers to any technical counterpart of the mobile test reader 100.

Accordingly, a non-exhaustive list of the external entity 104 related to the test 102 comprises at least one of the following: a manufacturer 300 of the mobile test reader 100, a distributor 302 of the mobile test reader 100, a manufacturer 304 of the test 102, a distributor 306 of the test 102, a health-care organization 308, a service provider 310.

The computing resource 800 may be implemented as a single server computer 312 or as a cluster of computers. The server 312 is a part of the client-server computing model that acts as distributed application which partitions tasks or workloads between the provider of a resource or service, called server 312, and the service requester, called client. The server 312 may serve both the mobile test reader 100 and the external entity 104. The server computer 312 is a host that is running one or more server programs which share their resources with clients 100, 104. The client 100, 104 may request a server's content or service function. The client 100, 104 therefore initiates a communication session with the server 312 which awaits incoming requests.

The computing resource 800 may also operate according to the cloud computing model 314.

Additionally, or alternatively, the computing resource 800 may also operate according to the peer-to-peer (P2P) computing model. A pure peer-to-peer system consists of equal peer nodes that simultaneously function as both clients 100 and servers 312. In a hybrid peer-to-peer system, a need for a special role is recognized: one or several nodes, but not all nodes, have a special role, which serves the other nodes of the peer-to-peer system. In FIG. 8, the server 800 may have the special role serving the client 100. Additionally, the client 100 may also serve as a server to another client 100.

Naturally, besides these example embodiments of the computing resource 800, other feasible computing architectures may be utilized as well to implement the hardware and software of the computing resource 800. Consequently, besides operating according to the client/server architecture, push technology may be utilized as well. In push technology, the request for a transaction is initiated by the server 312, whereas with the pull technology the request for the information is initiated by the client 100, 104.

Figure 10:
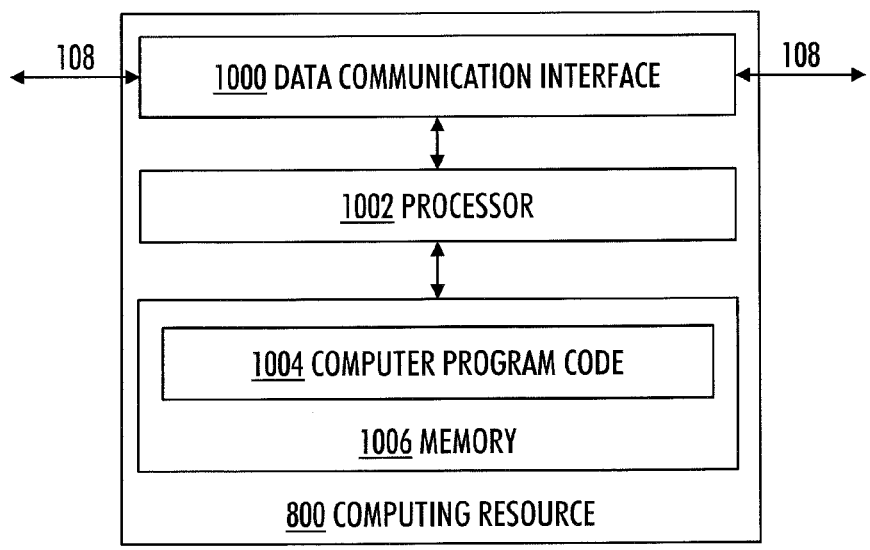
FIG. 10 illustrates example embodiments of a computing resource.

As illustrated in FIG. 10, the computing resource 800 comprises a data communication interface 1000, one or more processors 1002, and one or more memories 1006 including computer program code 1004. The implementation of these parts may follow the general principles illustrated in FIG. 6 for the implementation of the computer functionality, changing those things which need to be changed.

The data communication interface 1000 may utilize wireless and/or wired network interface technology. Consequently, the data communication interface 1000 may comprise a network interface card (also known as a network interface controller, a network adapter, or a LAN adapter) which couples the server computing resource to a telecommunications network. In an example embodiment, the data communication interface 1000 operates according to the Ethernet standard, TCP/IP or some other telecommunications standard. Alternatively or additionally, the data communication interface 1000 may be interoperable with a cellular network, in which case the data communication interface 1000 implements a radio modem capable of sending and receiving text messages, and/or transmitting packet data, over a radio link. Either way, the data communication interface 1000 may allow access to the Internet.

As was explained earlier, the test 102 may comprise chemical substances that will age, and as a result of the aging, the test criteria may change or become invalid. Accordingly, the tests 102 need to be manufactured under a strict quality control, so that every manufacturing batch will fulfil the set criteria. Due to the nature of the test substances (mostly organic) and substrate material (paper) there is a natural variation from one manufacturing batch to another batch.

If it were not possible to update parameters (such as test instructions and criteria) relating to the test result generation, very strict approval criteria would be required for manufactured test batches, and very narrow test criteria would only be allowed. By using to be described test-batch related parameters and their update to the mobile test readers 100, it will be possible to improve the test 102 quality and improve manufacturing yield of the tests 102.

The idea is to implement the computing resource 800 keeping a record of manufacturers' test 102 batches made and test 102 parameters related to each test 102 batch made. Such test 102 parameters may comprise minimum and maximum intensities of the stripes, the location of the stripes related to the test window 200, tolerances of the locations of the stripes, the relation of the width and length of the test window 200, for example. One parameter may be a formula (or a standard curve) describing the relation of the stripes to the result of the test 102: if relation of T and C stripes is three, the test 102 result, a CRP value is 24 mg/l. In another example embodiment, the test 102 reading time, starting after a sample has been set to the test 102, is monitored. The reading instructions may show that reading needs to be made between 4 minutes 30 seconds and 5 minutes 30 seconds. If the exact point in time is measured and recorded, it may help to find out how critical the timing is, and possibly give a correction formula dependent of a reading time to make the result reading more accurate. Or the information may just be used for accepting or rejecting the test 102 reading result. The test 102 parameters may also include the test 102 result generated by the mobile test reader 100 and another (subjective) test 102 result obtained by visual inspection of the output area 200 by the user.

The computing resource 800 shares the test 102 batch related parameters wirelessly to the mobile test readers 100. The computing resource 800 also obtains feedback from the mobile test readers 100. The computing resource 800 will process the data in order to provide feedback to the manufacturers of the tests 102 and/or to the other interested parties. Feedback data of used tests 102 may be analysed with different parameters such as time, location, test person identifier, test person age, test person sex, symptoms of the test person etc., mobile test reader 100 identifier, type of the mobile test reader 100, number of tests 102 used, number of tests 102 failed etc.

With this kind of processing, the manufacturers may follow the way the tests 102 are used, and whether they worked. The test 102 parameters may also be changed, if it is found out that a certain test 102 requires tuning or recalibration. The intensity of the stripes read may be followed, for example. As this is reported to the test manufacturer, the manufacturer may control its manufacturing process and the test 102 quality. Furthermore, the mobile test reader 100 instructions may be tuned according to this information. The external entity 104 may have also other ways to control the test 102 and test 102 reading quality. In an example embodiment, the mobile test reader 100 results are compared (weekly or monthly, for example) to more accurate laboratory testing results for some samples. This laboratory test result related to the test result read by the mobile test reader 100 may be reported to the computing resource 800, and further to the manufacturer.

Furthermore, even though the test parameters 102 normally are constant and cannot be changed online in the field, the described processing enables online updates in the field.

The test 102 or its container 210 may include a reference map/table to which the output area 200 of the test 102 is compared. The test reference map/table may be related to each test 102 batch manufactured, and it may be further calibrated with the described online communication.

Figure 11:
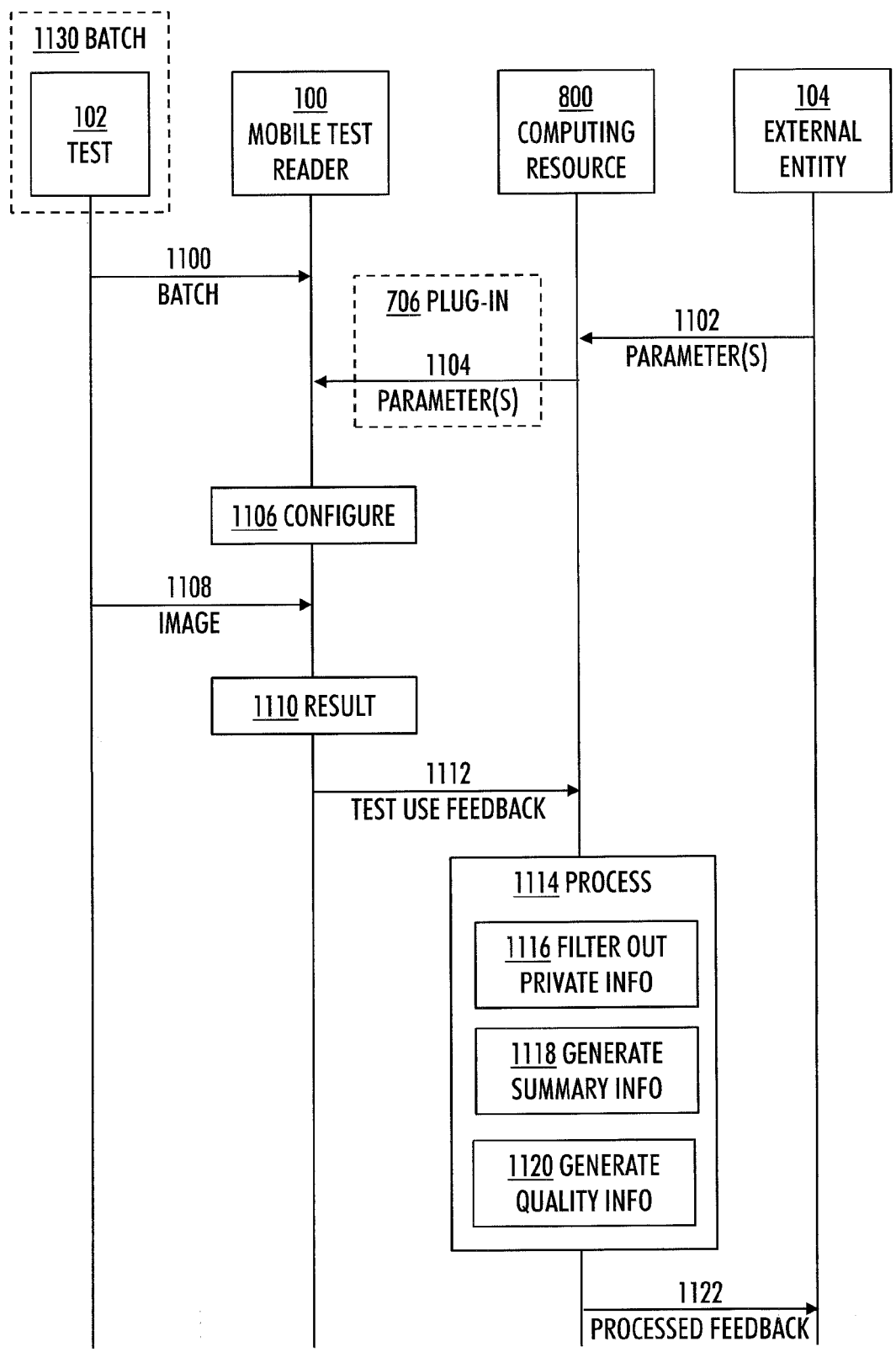
FIG. 11 illustrates further example embodiments of the mobile test reader, and example embodiments of a computing resource.

Next, with reference to FIG. 11, let us study example embodiments of the mobile test reader 100 and the computing resource 800 in the form of a signal sequence chart. Other functions, not described in this application, may also be executed between the operations or within the operations. Some of the operations or parts of the operations may also be left out or replaced by a corresponding operation or part of the operation. Note also that example embodiments described earlier, and especially in FIG. 7, may be used to supplement the example embodiments to be described.

The one or more memories 1006 and the computer program code 1004 of the computing resource 800 are configured to, with the one or more processors 1002, cause the computing resource 800 to receive, from the external entity 104 related to the test 102, with the data communication interface 1000, at least one parameter 1102 relating to test result generation of the test 102 belonging to a certain manufacturing batch 1130, and transmit, with the data communication interface 1000, the at least one parameter 1104 to at least one mobile test reader apparatus 100.

The one or more memories 418 and the computer program code 412 of the mobile test reader 100 are configured to, with the one or more processors 410, cause the mobile test reader 100 to receive, from the computing resource 800, with the wireless transceiver 406, at least one parameter 1104 relating to test result generation of the test 102 belonging to the certain manufacturing batch 1130, configure 1106 the test reader application 502 with the received at least one parameter 1104, take, with the digital camera 402 controlled by the test reader application 502 configured with the at least one parameter 1104, image data 1108 depicting the output area 200 of the test 102, and transmit, with the wireless transceiver 406, test use feedback 1112 to the computing resource 800.

In an example embodiment, the manufacturing batch 1130 may comprise one or more tests 102. The manufacturing batch 1130 may be determined according to the manufacturing date: tests 102 manufactured on a certain date form one manufacturing batch 1130, for example. The manufacturing batch 1130 may also be determined according to the number of manufactured tests: a predetermined number of tests 102 form one manufacturing batch 1130, for example. The manufacturing batch 1130 may also be determined according to the package size. Naturally, the manufacturing batch 1130 may also be determined by a combination of various properties. In any case, the manufacturing batch 1130 is such that the manufacturer is able to identify specific properties as relating to a certain manufacturing batch 1130, and that each test 102 is mapped to a manufacturing batch 1130.

In an example embodiment, the one or more memories 418 and the computer program code 412 of the mobile test reader 100 are configured to, with the one or more processors 410, cause the mobile test reader 100 to receive, with the wireless transceiver 406, the at least one parameter 1104 as a part of the test-specific plug-in 706 received from the computing resource 800.

In an example embodiment, the one or more memories 418 and the computer program code 412 of the mobile test reader 100 are configured to, with the one or more processors 410, cause the mobile test reader 100 to input, with the digital camera 402 or with the user interface 404, or with a wireless reading 408, information 1100 identifying the manufacturing batch 1130 of the test 102 to the test reader application 502.

In an example embodiment, the one or more memories 418 and the computer program code 412 of the mobile test reader 100 are configured to, with the one or more processors 410, cause the mobile test reader 100 to transmit, with the wireless transceiver 406, the image data 1108 as a part of the test use feedback 1112.

In an example embodiment, the one or more memories 418 and the computer program code 412 of the mobile test reader 100 are configured to, with the one or more processors 410, cause the mobile test reader 100 to generate, with the test reader application 502 configured with the at least one parameter 1104, a test result 1110 for the test 102 on the basis of the image data 1108, and transmit, with the wireless transceiver 406, the test result 1110 as a part of the test use feedback 1112 to the computing resource 800.

In an example embodiment, the one or more memories 1006 and the computer program code 1004 of the computing resource 800 are configured to, with the one or more processors 1002, cause the computing resource 800 to receive, with the data communication interface 1000, test use feedback 1112 from the at least one mobile test reader apparatus 100, process 1114 the received test use feedback 1112, and transmit, with the data communication interface 1000, the processed test use feedback 1122 to the external entity 104.

The processing 1114 of the test use feedback 1112 may relate to various aspects of the test 102 and the mobile test reader 100. Different kind of data mining methods, neural networks, and SOM (self-organizing maps), for example, may effectively be used for finding out different kind of valuable information from the test use feedback 1122. In an example embodiment, a neural network may learn from the test 102 images 106 which kind of test features are strong (stripes of the test window 200 or corners of the test window 200) or which kind of errors or uncertainties (uneven colouring in the output area 200, for example) are detected. In an example embodiment, the external entity 104 such as a doctor treating the test 102 user may order that the test 102 is to be repeated, and this information may be passed via the computing resource 800 back to the mobile test reader 100.

In an example embodiment, the one or more memories 1006 and the computer program code 1004 of the computing resource 800 are configured to, with the one or more processors 1002, cause the computing resource 800 to perform at least one of the following: filter out 1116 private patient identifying information for the processed test use feedback 1122; filter out 1116 confidential information for the processed test use feedback 1122; generate 1118 summary information for the processed test use feedback 1122; generate 1120 quality information comparing different manufacturing batches 1130 of the test 102 and/or different manufacturers of the test 102 for the processed test use feedback 1122.

The confidential information that is filtered out may comprise manufacturer-specific quality information of a manufacturer other than to which manufacturer the processed test use feedback 1122 will be transmitted. Such information, however, may in some cases be used in summaries or comparisons delivered to various interested parties 104.

The private patient identifying information that is filtered out may comprise patient's name, patient's social security number or other (unique) identifier, or his/her precise date of birth, for example.

The summary information may comprise the number of used tests 102 and the points in time when the tests 102 were taken, the number of positive and negative tests 102 related with the point in time when the tests 102 were taken, manufacturing batch 1130 related results (positives and negatives), for example The quality information may comprise the number of successful and failed tests 102, comparison of the test 102 results between different manufacturing batches 1130, number of positive and negative results in each manufacturing batch 1130, comparison of test 102 results of a specific manufacturing batch 1130 to average test 102 results, for example.

It will be obvious to a person skilled in the art that, as technology advances, the inventive concept can be implemented in various ways. The invention and its embodiments are not limited to the example embodiments described above but may vary within the scope of the claims.

The invention claimed is:

1. A computing resource comprising:
   a data communication interface;
   one or more processors; and
   one or more memories including computer program code, wherein the computing resource processes information relating to a test comprising at least one of the following: a lateral flow test and a test of at least one chemical property that affects the visual appearance of an output area of the test, and
   the one or more memories and the computer program code are configured to, with the one or more processors, cause the computing resource at least to:
      receive, from an external entity related to the test, with the data communication interface, one or more of at least one instruction and at least one criterion parameter relating to test result generation of the test belonging to a certain manufacturing batch, the external entity related to the test comprising at least one of the following: a manufacturer of the mobile test reader apparatus, a distributor of the mobile test reader apparatus, a manufacturer of the test, a distributor of the test, a health-care organization, and a service provider, and
      transmit, with the data communication interface, the one or more of the instruction and the criterion parameter to at least one mobile test reader apparatus thereby enabling an online update of the mobile test reader apparatus in the field with respect to the test belonging to the certain manufacturing batch requiring tuning or recalibration based on feedback regarding use and results of tests from mobile test readers.

2. The computing resource of claim 1, wherein the one or more memories and the computer program code are further configured to, with the one or more processors, cause the computing resource to:
   receive, with the data communication interface, test use feedback from the at least one mobile test reader apparatus,
   process the received test use feedback, and
   transmit, with the data communication interface, the processed test use feedback to the external entity.

3. The computing resource of claim 1, wherein the one or more memories and the computer program code are further configured to, with the one or more processors, cause the computing resource to perform at least one of the following:
   filter out private patient identifying information for the processed test use feedback,
   filter out confidential information for the processed test use feedback,
   generate summary information for the processed test use feedback, and
   generate quality information comparing one or more of different manufacturing batches of the test and different manufacturers of the test for the processed test use feedback.

4. The computing resource of claim 1, wherein the one or more memories and the computer program code are further configured to, with the one or more processors, cause the computing resource to:
   determine an intensity of stripes of the test that is read, and
   perform the tuning or recalibration based on the determined intensity.

5. The computing resource of claim 1, wherein the one or more memories and the computer program code are further configured to, with the one or more processors, cause the computing resource to:
   compare the mobile test reader results with laboratory testing results determined for a plurality of samples, and
   perform the online update based on the comparison.

6. The computing resource of claim 1, wherein the online update is performed by calibrating a reference map/table, to which the output area of the test is compared, the reference map/table being included in the test or a container of the test.

7. A mobile test reader apparatus comprising:
   a digital camera;
   a wireless transceiver;
   a user interface;
   one or more processors; and
   one or more memories including computer program code, wherein the mobile test reader apparatus processes information relating to a test comprising at least one of the following: a lateral flow test and a test of at least one chemical property that affects the visual appearance of an output area of the test, and
   the one or more memories and the computer program code are configured to, with the one or more processors, cause the mobile test reader apparatus at least to:
      receive, from a computing resource, with the wireless transceiver, one or more of at least one instruction and at least one criterion parameter relating to test result generation of a test belonging to a certain manufacturing batch,
      configure a test reader application with the received one or more of the instruction and the criterion parameter thereby enabling an online update of the mobile test reader apparatus in the field with respect to the test belonging to the certain manufacturing batch requiring tuning or recalibration based on feedback regarding use and results of tests from mobile test readers,
      take, with the digital camera controlled by the test reader application configured with the one or more of the instruction and the criterion parameter, image data depicting an output area of the test, and transmit, with the wireless transceiver, test use feedback to the computing resource, the test use feedback comprising one or more of the image data and a test result for the test generated with the test reader application configured with the one or more of the instruction and the criterion parameter on the basis of the image data.

8. The mobile test reader apparatus of claim 7, wherein the one or more memories and the computer program code are further configured to, with the one or more processors, cause the mobile test reader apparatus to:

receive, with the wireless transceiver, the one or more of the instruction and the criterion parameter as a part of a test-specific plug-in received from the computing resource.

9. The mobile test reader apparatus of claim 7, wherein the one or more memories and the computer program code are further configured to, with the one or more processors, cause the mobile test reader apparatus to:

input, with the digital camera or with the user interface, or with a wireless reading, information identifying the manufacturing batch of the test to the test reader application.

10. The mobile test reader apparatus of claim 7, wherein the mobile test reader apparatus comprises at least one of the following: a mobile phone, a smartphone, a tablet computer, and a general-purpose mobile computing device.

11. The computing resource of claim 7, wherein the one or more memories and the computer program code are further configured to, with the one or more processors, cause the mobile test reader apparatus to:

determine an intensity of stripes of the test that is read, and perform the tuning or recalibration based on the determined intensity.

12. The computing resource of claim 7, wherein the one or more memories and the computer program code are further configured to, with the one or more processors, cause the mobile test reader apparatus to:

compare the mobile test reader results with laboratory testing results determined for a plurality of samples, and perform the online update based on the comparison.

13. The computing resource of claim 7, wherein the online update is performed by calibrating a reference map/table, to which the output area of the test is compared, the reference map/table being included in the test or a container of the test.

\* \* \* \* \*